United States Patent [19]
Thomson et al.

[11] Patent Number: 6,060,453
[45] Date of Patent: May 9, 2000

[54] IMMUNOMODULATORY, ANTI-INFLAMMATORY, AND ANTI-PROLIFERATIVE COMPOUNDS: 5,6-DIDEOXY, 5-AMINO DERIVATIVES OF IDOSE AND 6-DEOXY, 6-AMINO DERIVATIVES OF GLUCOSE

[75] Inventors: David S. Thomson, Newbury Park, Calif.; Mary A. Korpusik, Branford, Conn.; Thomas P. Lawler, III, North Wales, Pa.

[73] Assignee: Greenwich Pharmaceuticals Incorporated, Ft. Washington, Pa.

[21] Appl. No.: 09/394,434

[22] Filed: Sep. 13, 1999

Related U.S. Application Data

[63] Continuation of application No. 08/938,019, Sep. 12, 1997, abandoned, which is a continuation of application No. 08/537,288, Sep. 29, 1995, abandoned, which is a continuation of application No. 08/257,258, Jun. 8, 1994, abandoned, which is a continuation-in-part of application No. 08/075,323, Jun. 11, 1993, abandoned.

[51] Int. Cl.$^7$ ............................. A61K 31/70; C07H 15/00
[52] U.S. Cl. ..................... 514/25; 536/17.2; 536/17.3
[58] Field of Search ............................. 514/25; 536/17.2, 536/17.3

[56] References Cited

U.S. PATENT DOCUMENTS

| | | | |
|---|---|---|---|
| Re. 30,354 | 7/1980 | Gordon | 536/4 |
| Re. 30,379 | 8/1980 | Gordon | 536/4 |
| Re. 32,268 | 10/1986 | Gordon | 514/25 |
| Re. 33,000 | 7/1989 | Gordon | 514/25 |
| 2,715,121 | 8/1955 | Glen et al. | 536/120 |
| 3,939,145 | 2/1976 | Gordon | 536/17.9 |
| 3,939,146 | 2/1976 | Gordon | 260/210 R |
| 3,965,262 | 6/1976 | Gordon | 424/180 |
| 4,016,261 | 4/1977 | Gordon | 424/180 |
| 4,017,608 | 4/1977 | Gordon | 424/180 |
| 4,056,322 | 11/1977 | Gordon et al. | 536/4 |
| 4,192,868 | 3/1980 | Tronchet et al. | 424/180 |
| 4,251,520 | 2/1981 | Bruzzese et al. | 424/180 |
| 4,273,766 | 6/1981 | Stanek | 424/180 |
| 4,497,649 | 2/1985 | Loh | 71/88 |
| 4,521,240 | 6/1985 | Loh | 71/88 |
| 4,554,011 | 11/1985 | Loh | 71/88 |
| 4,735,934 | 4/1988 | Gordon | 514/25 |
| 4,738,953 | 4/1988 | Gordon | 514/25 |
| 4,994,572 | 2/1991 | Fleet | 546/220 |
| 4,996,195 | 2/1991 | Ronsen et al. | 514/23 |
| 5,010,058 | 4/1991 | Ronsen et al. | 514/23 |
| 5,157,024 | 10/1992 | Gordon | 514/23 |
| 5,200,523 | 4/1993 | Fleet | 546/220 |
| 5,248,779 | 9/1993 | Fleet | 546/242 |
| 5,298,494 | 3/1994 | Arora et al. | 514/23 |
| 5,360,794 | 11/1994 | Arora | 514/25 |
| 5,367,062 | 11/1994 | Arora | 514/25 |

FOREIGN PATENT DOCUMENTS

| | | |
|---|---|---|
| WO 92/04359 | 3/1992 | WIPO . |
| WO 92/14745 | 9/1992 | WIPO . |
| WO 93/13117 | 7/1993 | WIPO . |

OTHER PUBLICATIONS

Chemical Abstract Structure Search Conducted By The Applicants. (Feb. 1993).

Z. Ahmed et al., Triflate Induced C–N Coupling of Sugars With Heterocyclic Bases: Synthesis of A New Class of Compounds, Synthetic Communications, 18(5), 501–505, (1988).

C.F. Gibbs et al., *J. Chem. Soc. D. Chem. Commun. 1969*, 20, p. 1210.

C.F. Gibbs et al., *Carbohyd. Res.*, 1970, 15, pp. 29–34.

M.R. Callstrom et al., *Mat. Res. Soc. Symp. Proc.*, 1990, 174, pp. 259–266.

*Primary Examiner*—Kathleen K. Fonda
*Attorney, Agent, or Firm*—Morgan, Lewis & Bockius LLP

[57] ABSTRACT

Compounds of this invention are 5,6-dideoxy, 5-amino derivatives of idose and 6-deoxy, 6-amino derivatives of glucose which exhibit immunomodulatory, anti-inflammatory, and anti-proliferative activity. Methods of preparation, pharmaceutical compositions containing the compounds and methods of treating inflammatory and/or autoimmune disorders employing the compounds are disclosed.

19 Claims, No Drawings

IMMUNOMODULATORY, ANTI-INFLAMMATORY, AND ANTI-PROLIFERATIVE COMPOUNDS: 5,6-DIDEOXY, 5-AMINO DERIVATIVES OF IDOSE AND 6-DEOXY, 6-AMINO DERIVATIVES OF GLUCOSE

CONTINUING DATA

This is a continuation of application Ser. No. 08/938,019, filed on Sep. 12, 1997, now abandoned, which is a continuation of Ser. No. 08/537,288, filed on Sep. 29, 1995, now abandoned, which is a continuation of Ser. No. 08/257,258, filed on Jun. 8, 1994, now abandoned, which is a continuation-in-part of Ser. No. 08/075,323 filed on Jun. 11, 1993, now abandoned.

BACKGROUND OF THE INVENTION

1. Field of the Invention

This invention relates to deoxy, amino derivatives of idose and glucose which exhibit immunomodulatory, anti-inflammatory, and anti-proliferative activity. Compounds of the invention are useful for treating mammals with inflammatory and/or autoimmune disorders. This invention also relates to pharmaceutical compositions containing the disclosed compounds and to methods of a treating inflammatory and/or autoimmune disorders employing the disclosed compounds.

2. Description of the Related Art

Derivatives of certain monosaccharides are known to have therapeutic value in the treatment of inflammatory and autoimmune disorders. Preparation of derivatives of these sugars can generally be accomplished by synthetic techniques which are known in the art.

To prepare derivatives of the monosaccharides, it is common to block or protect one or more of the hydroxyl groups with acetal blocking groups such as isopropylidene or cyclohexylidene groups and leave only one or two hydroxyl groups free to undergo further reaction. Various blocking groups and methods are described in U.S. Pat. Nos. 2,715,121 and 4,056,322 and the disclosures of these patents are incorporated herein by reference. For example, to prepare a derivative of α,D-glucose which is blocked in its furanose ring structure, the 1,2- and 5,6-hydroxyl groups can be blocked using an isopropylidene blocking group and the 3-position left open to undergo further reaction. After the reaction to derivatize the 3-position is complete, the blocking groups may be selectively removed to allow for further derivatization at other positions if desired.

Various derivatives of monosaccharides, as well as synthetic methods for their preparation, are described in U.S. Pat. Nos. Re. 30,354, Re. 30,379, Re. 32,268, 4,056,322, 4,735,934, 4,738,953, 4,996,195, 5,010,058, and 5,298,494. The therapeutic activity of various monosaccharides and their derivatives is also disclosed in these documents. The disclosures of these documents are incorporated herein by reference.

Two well known derivatives of α,D-glucose having beneficial therapeutic properties are amiprilose, which is 1,2-O-Isopropylidene-3-O-3'-(N,N'-dimethylamino-n-propyl)-α, D-glucofuranose, and its hydrochloric acid salt, amiprilose HCl (THERAFECTIN®). These compounds are known to have anti-inflammatory activity and demonstrate utility in managing the signs and symptoms of rheumatoid arthritis. More generally, these compounds have activity as immunomodulators, and therefore have a therapeutic effect on autoimmune disorders such as, for example, rheumatoid arthritis and psoriasis.

Deoxy derivatives of 1,2-O-Isopropylidene-α,D-glucofuranose are described in U.S. Pat. No. 5,010,058, the disclosure of which is incorporated herein by reference. That patent describes methods of preparing deoxy derivatives of 1,2-0-Isopro-pylidene-α, D-glucofuranose, and the use of such compounds in treating mammals with inflammatory and/or autoimmune disorders.

While some prior art monosaccharide derivatives have shown beneficial therapeutic activity, high doses of such compounds may often be needed to be effective and produce the desired results. Because therapy for inflammatory and autoimmune disorders is often chronic, there is a continuing need to develop potent, nontoxic compounds which can be orally administered to promote ease of treatment and patient compliance.

The present invention, therefore, is directed to new compounds and pharmaceutical compositions that exhibit greater potency than available compounds and compositions.

The present invention is also directed to a method of treating an animal or human suffering from an inflammatory and/or autoimmune disorder.

Other advantages of the invention are set forth in the description which follows, will be apparent from the description, or may be learned by practice of the invention.

SUMMARY OF THE INVENTION

To achieve the above objects, and in accordance with the purpose of the invention as embodied and broadly described here, there is provided:

A 5,6-dideoxy, 5-amino derivative of idose of the formula (I):

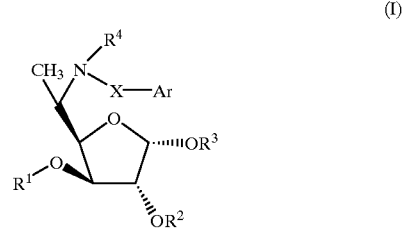

wherein

R$^1$ is a C$_3$ to C$_{15}$ branched or unbranched alkyl group, or an alkyl-cycloalkyl group;

R$^2$ and R$^3$ together with the atoms carrying them form an acetal protecting group;

Ar is a substituted or unsubstituted, aromatic or heteroaromatic group selected from the group consisting of imidazolyl, furanyl, pyrrolyl, 1,3-benzodioxol-5-ylmethyl, pyridinyl, thienyl, naphthyl, and phenyl;

R$^4$ is hydrogen or a branched or unbranched lower alkyl group having 1 to 5 carbon atoms; and X is a bond, or a branched or unbranched lower alkylene group having 1 to 5 carbon atoms, or together with R$^4$, and the nitrogen carrying them, forms a 5-, 6-, or 7-membered heterocycle fused to the aromatic or heteroaromatic group Ar;

or a physiologically acceptable salt thereof.

A 6-deoxy, 6-amino derivative of glucose of the formula (II):

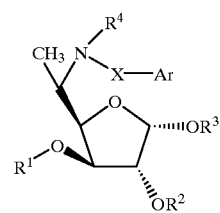

(I)

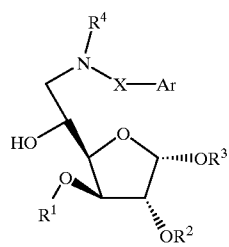

(II)

wherein $R^1$ is a $C_3$ to $C_{15}$, branched or unbranched alkyl group, or an alkyl-cycloalkyl group;

$R^2$ and $R^3$ together with the atoms carrying them form an acetal protecting group;

Ar is a substituted or unsubstituted, aromatic or heteroaromatic group selected from the group consisting of imidazolyl, furanyl, pyrrolyl, 1,3-benzodioxol-5-ylmethyl, pyridinyl, thienyl, naphthyl, and phenyl;

$R^4$ is hydrogen or a branched or unbranched lower alkyl group having 1 to 5 carbon atoms; and X is a bond, or a branched or unbranched lower alkylene group having 1 to 5 carbon atoms, or together with $R^4$, and the nitrogen carrying them, forms a 5-, 6-, or 7-membered heterocycle fused to said aromatic or heteroaromatic group Ar;

or a physiologically acceptable salt thereof.

The immunomodulatory, anti-proliferative, and/or anti-inflammatory compounds of formulae I and II exhibit beneficial therapeutic properties and are useful in the treatment of inflammatory and autoimmune disorders. Specifically, these compounds have demonstrated inhibitory effects on lymphocyte proliferation, immunomodulatory, and anti-inflammatory activity in art recognized in vitro and ex vivo screening tests. Compounds having this activity are useful, for example, in treating animals and humans with various chronic inflammatory and/or autoimmune conditions such as, but not limited to, rheumatoid arthritis, psoriasis, psoriatic arthritis, scleroderma, systemic lupus erythematosus, multiple sclerosis,.inflammatory bowel disease, osteoarthritis, and asthma.

The present invention also provides pharmaceutical compositions containing the subject 5,6-dideoxy, 5-amino-derivatives of idose or 6-deoxy, 6-amino-derivatives of glucose, and methods for the treatment of inflammatory and/or autoimmune disorders employing those compounds. The pharmaceutical compositions comprise an effective amount of at least one of these compounds or a physiologically tolerated salt thereof, with a pharmaceutically acceptable carrier.

DETAILED DESCRIPTION OF THE INVENTION

In one embodiment, the compounds of this invention are 5,6-dideoxy, 5-amino derivatives of idose and physiologically acceptable salts thereof. These compounds may be represented by formula (I):

$R^1$ is selected from a $C_3$ to $C_{15}$ branched or unbranched alkyl group, and an alkyl-cycloalkyl group. Preferably, $R^1$ is a $C_4$ to $C_{12}$ unbranched alkyl or $(C_1-C_3)$-alkyl-$(C_3-C_7)$ -cycloalkyl group. Most preferably, $R^1$ is pentyl, heptyl, decyl, dodecyl, cyclopropylmethyl, cyclohexylmethyl or cyclohexylpropyl.

$R^2$ and $R^3$ together with the atoms carrying them form an acetal protecting group. Preferably, the acetal protecting group is an isopropylidene group or a cyclohexylidene group. Most preferably, $R^2$ and $R^3$ form an isopropylidene group.

The group Ar is a substituted or unsubstituted, aromatic or heteroaromatic group selected from pyridinyl, furanyl, thienyl, pyrrolyl, 1,3-benzodioxol-5-ylmethyl, naphthyl, and phenyl.

Preferred groups for Ar are pyridinyl and substituted or unsubstituted phenyl of the formula:

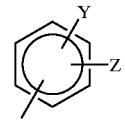

Y and Z are each independently H, F, Cl, Br, $OCH_3$, CN, $NO_2$, $CF_3$, $OCF_3$ or NR'R", wherein R' and R", which may be the same or different, are a branched or non-branched alkyl group, preferably having 1 to 6 carbon atoms,, which may be substituted or non-substituted. Particularly preferred are compounds where X and Ar together form a group selected from 2-pyridinyl, 4-pyridinyl, (2-pyridinylmethyl), (2-pyridinylethyl), (2-furanylmethyl), 1,2,3,4-tetrahydroisoquinolinyl, (2-fluorophenyl)methyl, (4-pyridinylmethyl), (3-methoxyphenyl)methyl, 3-(N-imidazolyl) propyl, (4-chlorophenyl)methyl, (3-chlorophenyl)methyl, (2-chlorophenyl)methyl, (4-fluorophenyl)methyl, (3-fluorophenyl) methyl, (4-bromophenyl)methyl, (4-trifluoromethylphenyl)methyl, (4-trifluoromethoxyphenyl)methyl, (2,4-dichlorophenyl) methyl, (2,4-difluorophenyl)methyl, (2,3-dimethoxyphenyl) methyl, and (3,5-dimethoxyphenyl)methyl.

$R^4$ is a hydrogen or a branched or unbranched lower alkyl group having 1 to 5 carbon atoms. Preferably, $R^4$ is hydrogen, methyl, ethyl or propyl and most preferably hydrogen or methyl.

The divalent group X is a bond or is selected from a branched or unbranched lower alkylene group having 1 to 5 carbon atoms or together with $R^4$, and the nitrogen carrying them, forms a 5-, 6-, or 7-member heterocycle fused to the aromatic or heteroaromatic group Ar. Preferably, when X is an alkylene group, it is a $C_1-C_4$ alkylene group. Most preferably, X is a bond, i.e., a bond joining Ar and N, or a methylene, ethylene, propylidene, or 2'-propylidene group. When X together with $R^4$, and the nitrogen carrying them, form a 5-, 6- or 7-member heterocyclic fused to the aromatic or heteroaromatic group Ar, the preferred group is a hydrogenated isoquinoline group, preferably tetrahydroisoquinolinyl. Preferred compounds of formula I include:

1,2-O-Isopropylidene-3-O-decyl-5,6-dideoxy-5-N-[(2-pyridinyl-methyl)amino]-β,L-idofuranose, (Ia);

1,2-O-Isopropylidene-3-O-decyl-5,6-dideoxy-5-N-[(2-furanylmethyl)amino]-β,L-idofuranose, (Ib);

1,2-O-Isopropylidene-3-O-decyl-5,6-dideoxy-5-N-[[2-(2-pyridinyl)ethyl]amino]-β,L-idofuranose, (Ic);

1,2-O-Isopropylidene-3-O-cyclohexylmethyl-5,6-dideoxy-5-N-[(4-pyridinylmethyl)amino]-β,L-idofuranose, (Id) and 1,2-O-Isopropylidene-3-O-cyclohexylmethyl-5,6-dideoxy-5-N-[(2-pyridinylmethyl)amino]-β,L-idofuranose, (Ie). Particularly preferred are compounds Ia and Ib.

According to another embodiment, this invention includes compounds which are 6-deoxy, 6-amino derivatives of glucose or physiologically acceptable salts thereof. These derivatives may be represented by formula II:

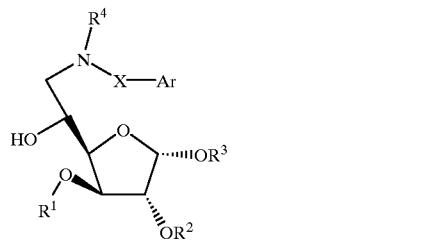

(II)

The groups $R^1$, $R^2$, $R^3$ and R4, Ar and X in formula II have the same meaning and preferred embodiments as described for formula I. Preferred compounds of formula II include:

1,2-O-Isopropylidene-3-O-decyl-6-deoxy-6-N-(1,2,3,4-tetrahydroisoquinolinyl)-α,D-glucofuranose, (IIa);

1,2-O-Isopropylidene-3-O-decyl-6-deoxy-6-N-[[(3,4-difluorophenyl)methyl]amino]-α,D-glucofuranose, (IIb);

1,2-O-Isopropylidene-3-O-heptyl-6-deoxy-6-N-[[(2-fluorophenyl)methyl]amino]-α,D-glucofuranose, (IIc);

1,2-O-Isopropylidene-3-O-heptyl-6-deoxy-6-N-[(2-pyridinylmethyl)amino]-α,D-glucofuranose, (IId);

1,2-O-Isopropylidene-3-O-heptyl-6-deoxy-6-N-[(2-pyridinylmethyl)amino]- α,D-glucofuranose hydrochloride, (IIe);

1,2-O-Isopropylidene-3-O-cyclohexylmethyl-6-deoxy-6-N-[(4-pyridinylmethyl)amino]-α,D-glucofuranose, (IIf);

1,2-O-Isopropylidene-3-O-cyclohexylmethyl-6-deoxy-6-N-[[(3-methoxyphenyl)methyl]amino]-α,D-glucofuranose, (IIg);

1,2-O-Isopropylidene-3-O-cyclohexylmethyl-6-deoxy-6-N-[[3-(N-imidazolyl)propyl]amino]-α,D-glucofuranose, (IIh);

1,2-O-Isopropylidene-3-O-dodecyl-6-deoxy-6-N-[[2-(2-pyridinyl)ethyl]amino]-α,D-glucofuranose, (IIi);

1,2-O-Isopropylidene-3-O-heptyl-6-deoxy-6-N-[(phenylmethyl)amino]-α,D-glucofuranose, (IIj);

1,2-O-Isopropylidene-3-O-heptyl-6-deoxy-6-N-[(3-pyridinylmethyl)amino]-α,D-glucofuranose, (IIk);

1,2-O-Isopropylidene-3-O-dodecyl-6-deoxy-6-N-[[4-(1-benzyl)piperidinyl]amino]-α,D-glucofuranose, (IIl);

1,2-O-Isopropylidene-3-O-dodecyl-6-deoxy-6-N-[[(2-trifluoromethylphenyl)methyl]amino]-α,D-glucofuranose, (IIm);

1,2-O-Isopropylidene-3-O-dodecyl-6-deoxy-6-N-[[(4-trifluoromethylphenyl)methyl]amino]-α,D-glucofuranose, (IIn);

1,2-O-Isopropylidene-3-O-dodecyl-6-deoxy-6-N-[[(3-trifluoromethylphenyl)methyl]amino]-α,D-glucofuranose, (IIo);

1,2-O-Isopropylidene-3-O-dodecyl-6-deoxy-6-N-[[2-(3-chlorophenyl)ethyl]amino]-α,D-glucofuranose, (IIp);

1,2-O-Isopropylidene-3-O-dodecyl-6-deoxy-6-N-[[2-(4-chlorophenyl)ethyl]amino]-α,D-glucofuranose, (IIq);

1,2-O-Isopropylidene-3-O-dodecyl-6-N-[[2-(2-chlorophenyl)ethyl]amino]-α,D-glucofuranose, (IIr);

1,2-O-Isopropylideneme3-O-heptyl-6-N-[[(2-methoxyphenyl)methyl]amino]-α,D-glucofuranose, (IIs);

1,2-O-Isopropylidene-3-O-heptyl-6-N-[[(3-methoxyphenyl)methyl]amino]-α,D-glucofuranose, (IIt);

1,2-O-Isopropylidene-3-O-heptyl-6-N-[[(4-methoxyphenyl)methyl]amino]-α,D-glucofuranose, (IIu);

1,2-O-Isopropylidene-3-O-dodecyl-6-deoxy-6-N-[[(4-fluorophenyl)methyl]amino]-α,D-glucofuranose, (IIv);

1,2-O-Isopropylidene-3-O-dodecyl-6-deoxy-6-N-[(2-thienymethyl)amino]-α,D-glucofuranose, (IIw);

1,2-O-Isopropylidene-3-O-heptyl-6-deoxy-6-N-[[(3-fluorophenyl)methyl]amino]-α,D-glucofuranose, (IIx);

1,2-O-Isopropylidene-3-O-heptyl-6-deoxy-6-N-[[2-(4-methoxyphenyl)ethyl]amino]-α,D-glucofuranose, (IIy);

1,2-O-Isopropylidene-3-O-heptyl-6-deoxy-6-N-[[(3-chlorophenyl)methyl]amino]-α,D-glucofuranose, (IIz);

1,2-O-Isopropylidene-3-O-heptyl-6-deoxy-6-N-[[(4-chlorophenyl)methyl]amino]-α,D-glucofuranose, (IIaa);

1,2-O-Isopropylidene-3-O-heptyl-6-deoxy-6-N-[[(2-chlorophenyl)methyl]amino]-α,D-glucofuranose, (IIbb);

1,2-O-Isopropylidene-3-O-cyclohexylmethyl-6-deoxy-6-N-[(phenylmethyl)amino]-α,D-glucofuranose, (IIcc);

1,2-O-Isopropylidene-3-O-heptyl-6-deoxy-6-N-[(3-phenylpropyl)amino]-α,D-glucofuranose, (IIdd);

1,2-O-Isopropylidene-3-O-heptyl-6-deoxy-6-N-[[(1-methyl-3-phenyl)propyl]amino]-α,D-glucofuranose, (IIee);

1,2-O-Isopropylidene-3-O-heptyl-6-deoxy-6-N-[[2-(1-methyl-pyrrol-2-yl)ethyl]amino]-α,D-glucofuranose, (IIff);

1,2-O-Isopropylidene-3-O-cyclohexylmethyl-6-deoxy-6-N-[[((4-fluorophenyl)methyl]amino]-α,D-glucofuranose, (IIgg);

1,2-O-Isopropylidene-3-O-cyclohexylmethyl-6-deoxy-6-N-[(2-pyridinylmethyl)amino]-α,D-glucofuranose, (IIhh);

1,2-O-Isopropylidene-3-O-decyl-6-deoxy-6-N-[(1,3-benzodioxol-5-ylmethyl)amino]-α,D-glucofuranose, (IIii);

1,2-O-Isopropylidene-3-O-heptyl-6-deoxy-6-N-[[(2,4-dichlorophenyl)methyl]amino]-α,D-glucofuranose, (IIjj);

1,2-O-Isopropylidene-3-O-heptyl-6-deoxy-6-N-[[(2,3-dimethoxyphenyl)methyl]amino]-α,D-glucofuranose, (IIkk);

1,2-O-Isopropylidene-3-O-heptyl-6-deoxy-6-N-[[(3,5-dimethoxyphenyl)methyl]amino]-α,D-glucofuranose, (IIll);

1,2-O-Isopropylidene-3-O-decyl-6-deoxy-6-N-[[(3,4-dichlorophenyl)methyl]amino]-α,D-glucofuranose, (IImm);

1,2-O-Isopropylidene-3-O-decyl-6-deoxy-6-N-[[(2,6-difluorophenyl)methyl]amino]-α,D-glucofuranose, (IInn);

1,2-O-Isopropylidene-3-O-(3'-cyclohexylpropyl)-6-deoxy-6-N-[(2-pyridinylmethyl)amino]-α,D-glucofuranose, (IIoo);

1,2-O-Isopropylidene-3-O-(3'-cyclohexylpropyl)-6-deoxy-6-N-[[(2-chlorophenyl)methyl]amino]-α,D-glucofuranose, (IIpp);

1,2-O-Isopropylidene-3-O-cyclohexylmethyl-6-deoxy-6-N-[[(2-chlorophenyl)methyl]amino]-α,D-glucofuranose, (IIqq);

1,2-O-Isopropylidene-3-O-cyclohexylmethyl-6-deoxy-6-N-[[(3-chlorophenyl)methyl]amino]-α,D-glucofuranose, (IIrr);

1,2-O-Isopropylidene-3-O-cyclohexylmethyl-6-deoxy-6-N-(1,2,3,4-tetrahydroisoquinolinyl)-α,D-glucofuranose, (IIss);

1,2-O-Isopropylidene-3-O-cyclohexylmethyl-6-deoxy-6-N-[(2-thienylmethyl) amino]-α,D-glucofuranose, (IItt);

1,2-O-Isopropylidene-3-O-cyclohexylmethyl-6-deoxy-6-N-[(1-naphthylmethyl)amino]-α,D-glucofuranose, (IIuu);

1,2-O-Isopropylidene-3-O-pentyl-6-deoxy-6-N-[(2-pyridinylmethyl)amino]-α,D-glucofuranose, (IIvv);

1,2-O-Isopropylidene-3-O-pentyl-6-deoxy-6-N-[[(2-chlorophenyl)methyl]amino]-α,D-glucofuranose, (IIww);

1,2-O-Isopropylidene-3-O-pentyl-6-deoxy-6-N-[[(3-chlorophenyl)methyl]amino]-α,D-glucofuranose, (IIxx);

1,2-O-Isopropylidene-3-O-cyclopropylmethyl-6-deoxy-6-N-[[(2-chlorophenyl)methyl]amino]-α,D-glucofuranose, (IIyy);

1,2-O-Isopropylidene-3-O-cyclopropylmethyl-6-deoxy-6-N-[[(3-chlorophenyl)methyl]amino]-α,D-glucofuranose, (IIzz);

1,2-O-Isopropylidene-3-O-cyclohexylmethyl-6-deoxy-6-N-[[(4-chlorophenyl)methyl]amino]-α,D-glucofuranose, (IIaaa);

1,2-O-Isopropylidene-3-O-cyclohexylmethyl-6-deoxy-6-N-[[(4-trifluoromethylphenyl)methyl]amino]-α,D-glucofuranose, (IIbbb);

1,2-O-Isopropylidene-3-O-cyclohexylmethyl-6-deoxy-6-N-[[(3-fluorophenyl)methyl]amino]-α,D-glucofuranose, (IIccc);

1,2-O-Isopropylidene-3-O-pentyl-6-deoxy-6-N-[[(4-fluorophenyl)methyl]amino]-α,D-glucofuranose, (IIddd);

1,2-O-Isopropylidene-3-O-cyclohexylmethyl-6-deoxy-6-N-[[(4-fluorophenyl)methyl]amino]-α,D-glucofuranose, (IIeee);

1,2-O-Isopropylidene-3-O-heptyl-6-deoxy-6-N-[[(4-fluorophenyl)methyl]amino]-α,D-glucofuranose, (IIfff);

1,2-O-Isopropylidene-3-O-cyclopropylmethyl-6-deoxy-6-N-[[(4-fluorophenyl)methyl]amino]-α,D-glucofuranose, (IIggg);

1,2-O-Isopropylidene-3-O-(3'-cyclohexylpropyl)-6-deoxy-6-N-[[(4-fluorophenyl)methyl]amino]-α,D-glucofuranose, (IIhhh);

1,2-O-Isopropylidene-3-O-cyclohexylmethyl-6-deoxy-6-N-[[(2,4-difluorophenyl)methyl]amino]-α,D-glucofuranose, (IIiii);

1,2-O-Isopropylidene-3-O-cyclohexylmethyl-6-deoxy-6-N-[[(4-trifluoromethoxyphenyl)methyl]amino]-α,D-glucofuranose, (iijjj);

1,2-O-Isopropylidene-3-O-heptyl-6-deoxy-6-N-(4-pyridinylamino)-α,D-glucofuranose, (IIkkk);

1,2-O-Isopropylidene-3-O-heptyl-6-deoxy-6-N-[(2-chlorophenyl)amino]-α,D-glucofuranose, (IIlll);

1,2-O-Isopropylidene-3-O-cyclohexylmethyl-6-deoxy-6-N-[[(3,4-difluorophenyl)methyl]amino]-α,D-glucofuranose, (IImmm);

1,2-O-Isopropylidene-3-O-cyclohexylmethyl-6-deoxy-6-N-[[(4-bromophenyl)methyl]amino]-α,D-glucofuranose,, (IInnn);

1,2-O-Isopropylidene-3-O-cyclohexylmethyl-6-deoxy-6-N-[(4-pyridinylmethyl)amino]-α,D-glucofuranose hydrochloride, (IIooo);

1,2-O-Isopropylidene-3-O-cyclohexylmethyl-6-deoxy-6-N-[[(3-methoxyphenyl)methyl]amino]-α,D-glucofuranose hydrochloride, (IIppp);

1,2-O-Isopropylidene-3-O-heptyl-6-deoxy-6-N-[[(2-chlorophenyl)methyl]amino]-α,D-glucofuranose hydrochloride, (IIqqq);

1,2-O-Isopropylidene-3-O-heptyl-6-deoxy-6-N-[[(3-chlorophenyl)methyl]amino]-α,D-glucofuranose hydrochloride, (IIrrr);

1,2-O-Isopropylidene-3-O-cyclohexylmethyl-6-deoxy-6-N-[[(4-fluorophenyl)methyl]amino]-α,D-glucofuranose hydrochloride, (IIsss); and 1,2-O-Isopropylidene-3-O-cyclohexylmethyl-6-deoxy-6-N-[(2-pyridinylmethyl)amino]-α,D-glucofuranose hydrochloride, (IIttt).

The following compounds are particularly preferred IIa, IIc, IId, IIe, IIf, IIg, IIh, IIz, IIbb, IIgg, IIhh, IIii, IIjj, IIkk, IIll, IIhhh, IIfff, IIggg, IIlll, IIooo, IIppp, IIqqq, IIrrr, IIsss and IIttt. Most preferred are compounds IIe, IIppp, IIqqq, IIrrr, IIsss, and IIttt.

The immunomodulatory, anti-proliferative and/or anti-inflammatory compounds of the present invention also include physiologically acceptable salts of the compounds of formulae (I) and (II). Preferred physiologically acceptable salts are acid-addition salts. Common physiologically acceptable acid-addition salts include but are not limited to, hydrochloric acid salts, oxalate salts and tartrate salts.

The compounds of the invention may be prepared according to a general synthetic procedure. The examples below demonstrate the general synthetic procedure, as well as the specific preparation, for compounds according to this invention. The examples are illustrative, and are not intended to limit, in any manner, the claimed invention.

The general synthetic procedure can be described as follows. First, a suitably protected hexofuranose having a free hydroxyl group is alkylated at that hydroxyl group with a base and an appropriate alkyl halide. Selective removal of a protecting group provides an intermediate which can be preferentially tosylated. If tosylated at the 6-position, the resulting tosylate is then displaced upon treatment with an appropriate primary or secondary amine to give the deoxy, 6-amino compounds of formula (II) directly. Alternatively, compounds having a tosylate group at the 6-position can be reduced with a suitable reducing agent to yield an intermediate which, upon a second tosylation at the 5-position and subsequent reaction with an appropriate primary or secondary amine gives compounds according to formula (I).

Pharmacologic Activity

Compounds of the present invention have demonstrated immunomodulatory, anti-inflammatory, and anti-proliferative effects in biological assays. Standard in vitro and ex vivo immunologic assays were performed on compounds of the present invention in order to assess immunomodulatory, anti-inflammatory, and anti-proliferative activity. These included the mouse Arachidonic Acid Ear assay, the ex vivo Macrophage Phagocytosis assay, the in vitro and ex vivo Mixed Lymphocyte Response (MLR), and the in vitro mouse Mitogen-Induced T Lymphocyte Proliferation assay.

The MLR functions as a test of immunomodulatory effects of the compounds whereby inhibitory effects on T lymphocyte activation and antigen presentation are determined. Further immunomodulatory effects were analyzed in an ex vivo Macrophage Phagocytosis assay.

Anti-proliferative effects were demonstrated by measuring the inhibitory effects of compounds of the present invention on the cellular proliferation of Concanavalin A stimulated murine splenocytes.

Anti-inflammatory effects were determined in a mouse Arachadonic Acid Ear assay.

Inflammation and mechanisms involved in the pathogenesis of autoimmune diseases involve cellular activation and proliferation as well as abnormal immune system activation. Therefore, the assays employed here are appropriate and accepted screens for novel compounds in the treatment of inflammatory and/or autoimmune disorders.

The compounds of the present invention have demonstrated immunomodulatory, anti-inflammatory, and anti-proliferative activities. Concentrations tested in in vitro assays ranged from 0.00001 to 10 µg/mL and 5 to 25 mg/kg in ex vivo assays. Compounds of the present invention uniformly demonstrated potent in vitro and ex vivo immunomodulatory and anti-proliferative effects. These results indicate that compounds of the present invention are highly active agents with potent in vitro and ex vivo activities.

The 5,6-dideoxy, 5-amino- derivatives of idose and 6-deoxy, 6-amino-derivatives of glucose of the invention are useful for treating animals and mammals with various chronic inflammatory and/or autoimmune conditions such as, but not limited to, rheumatoid arthritis, psoriasis, psoriatic arthritis, scleroderma, systemic lupus erythematosus, multiple sclerosis, inflammatory bowel disease, osteoarthritis, and asthma. Due to their valuable pharmacological properties, the compounds of the present invention or their physiologically acceptable salts, are particularly suitable for use as active compounds in pharmaceutical compositions for the treatment of, for example, rheumatic inflammatory disorders.

The compounds described above can either be administered alone in the form of microcapsules, in mixtures with one another, or in combination with acceptable pharmaceutical carriers. The invention, thus, also relates to pharmaceutical compositions which comprise an effective amount of at least one compound of the invention with or without a pharmaceutically or physiologically acceptable carrier. If appropriate, the compound may be administered in the form of a physiologically acceptable salt, for example, an acid-addition salt.

The present invention also encompasses a method of treating animals or humans suffering from one or more of the inflammatory and/or autoimmune disorders discussed above. This method comprises administering to the animal or person an effective amount of at least one of the compounds of the invention, or a physiologically acceptable salt thereof, with or without a pharmaceutically acceptable carrier. The compounds according to the invention can be administered orally, topically, rectally, anterally, internally, by boluses or, if desired, parenterally. Oral administration is preferred.

Suitable solid or liquid formulations are, for example, granules, powders, coated tablets, microcapsules, suppositories, syrups, elixirs, suspensions, emulsions, drops or injectable solutions. Also, the compounds of the invention may be employed in preparations having a protracted release of the active compound. Commonly used additives in protracted release preparations are excipients, disintegrates, binders, coating agents, swelling agents, glidants, or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, starch, cellulose and its derivatives, animal and vegetable oils, polyethylene glycols and solvents. Common solvents include sterile water and monohydric or polyhydric alcohols such as glycerol.

The pharmaceutical compositions are preferably produced and administered in dosage units, each unit containing as an active component an effective dose of at least one compound of the present invention and/or at least one of its physiologically acceptable salts. In the case of mammals, the effective dose to treat autoimmune and/or anti-inflammatory disorders can range from about 1 to 100 mg/kg of body weight per day.

EXAMPLES

The following examples demonstrate the preparation of compounds according to this invention. The examples are illustrative, and are not intended to limit, in any manner, the claimed invention.

Example 1

Preparation of 1,2-O-Isopropylidene-3-O-decyl-5,6-dideoxy-5-N-[(2-pyridinylmethyl)amino]-β,L-idofuranose (Ia)

Preparation of 1,2:5,6-Di-O-Isopropylidene-3-O-decyl-α,D-glucofuranose 1,2:5,6-Di-O-Isopropylidene-α,D-glucofuranose (101 g, 0.39 mol) was combined with dried, crushed sodium hydroxide (46.17 g, 1.1543 mol) and decylbromide (105.4 g, 0.4768 mol) in around bottom flask. The reaction was stirred at 127–130° C., and monitored by TLC (70% ether in hexane). After two hours the reaction was cooled. The mixture was extracted with ether, filtered, and concentrated. The compound was chromatographed on silica gel, eluting with 30% ether in hexane. The title compound was obtained in 96% yield (149 g).

Preparation of 1,2-O-Isopropylidene-3-O-decyl-α, D-glucofuranose 1,2:5,6-Di-O-Isopropylidene-3-O-decyl-α,D-glucofuranose (92 g) was dissolved in THF (95 mL) in a round bottom flask and cooled to 0–5° C., with stirring.

Perchloric acid (30% vol.) was added drop-wise to the solution at a rate of 1 drop/sec. The reaction was monitored by TLC (70% ether in hexane). After 25 minutes the reaction was quenched by drop-wise addition of a saturated potassium carbonate solution. The reaction mixture was diluted with THF. When the reaction reached a pH of 7–8, the reaction was filtered, and THF was evaporated. The resulting mixture was extracted with ether and the water removed by separatory funnel and magnesium sulfate. The organic layer was filtered and concentrated. The compound was chromatographed on silica gel, eluting with 30%–40% ether in hexane. The desired product was obtained in 68% yield (56.4 g).

Preparation of 1,2-O-Isopropylidene-3-O-decyl-6-O-tosyl-α,D-glucofuranose 1,2-O-Isopropylidene-3-O-decyl-α,D-glucofuranose (21.7 g, 0.0603 mol) was dissolved in pyridine in a round bottom flask equipped with a drying tube and cooled to 0–5° C. with stirring. Tosyl chloride (11.55 g, 0.0606 mol) was dissolved in pyridine (50 mL total) and added drop-wise to the solution at a rate of 1 drop/sec. The reaction was monitored by TLC (50% ether in hexane). After 2 hours the reaction was poured into ice water (50 mL) and extracted with ether. The organic layer was then washed three times each with water, saturated sodium bicarbonate, and brine. The organic layer was dried over magnesium sulfate, filtered, and concentrated. The compound was chromatographed on silica gel, eluting with 20% ether in hexane to ether. The desired tosylate was obtained in 87% yield (24.1 g). Some impurity remained, but the compound was usable in further synthesis.

Preparation of 1,2-O-Isopropylidene-3-O-decyl-6-deoxy-α,D-glucofuranose

Lithium Aluminum Byride (LAH) (3.62 g, 0.0953 mol) was placed in a round bottom flask equipped with a drying tube and cooled to 0–5° C. with stirring. Tetrahydrofuran (20 mL) was added drop-wise to the LAH at a rate of 1 drop/sec. (10 minute addition time). 1,2-O-Isopropylidene-3-O-decyl-6-O-tosyl-α,D-glucofuranose (24.5 g, 0.0477 mol) was dissolved in THF (35 mL, anhydrous) and added drop-wise to the slurry at a rate of 1 drop/sec. (1.5 hours addition time). The reaction was monitored by TLC (30% ether in hexane). After 86 minutes, the reaction was quenched by drop-wise addition of water (10 mL), then drop-wise addition of sodium hydroxide solution (10 mL, 15% wt.) The reaction was diluted with TEF and filtered. Tetrahydrofuran was removed, and the residue was dissolved in ether. Any residual water was removed by separatory funnel, then magnesium sulfate. The organic layer was filtered and concentrated. The compound was chromatographed on silica gel, eluting with 10% ether in hexane to ether. The title compound was obtained in 80% yield (13.2 g).

Preparation of 1,2-O-Isopropylidene-3-O-decyl-5-O-tosyl-6-deoxy-α,D-glucofuranose 1,2-O-Isopropylidene-3-O-decyl-6-deoxy-α,D-glucofuranose (13 g, 0.0378 mol) was combined with tosyl chloride (14.28 g, 0.0750 mol) and pyridine (20 mL) in a round bottom flask equipped with a drying tube. The reaction was stirred and monitored by TLC (80% ether in hexane). After 27 hours, the reaction was poured into ice water and extracted with ether. The organic layer was then washed three times each with water, saturated sodium bicarbonate, and brine. The organic layer was then dried over magnesium sulfate, filtered, and concentrated. The compound was chromatographed on silica gel and eluted with 10% ether in hexane. The title compound was obtained in 61% yield (11.5 g).

Preparation of 1,2-O-Isopropylidene-3-O-decyl-5,6-dideoxy-5-N-[(2-pyridinylmethyl)amino]-β,L-idofuranose (Ia)

1,2-O-Isopropylidene-3-O-decyl-5-O-tosyl-6-deoxy-α,D-glucofuranose (2.0 g) was combined with 2-(methylamino)-pyridine (8 mL) in a round bottom flask and stirred at 100° C. The reaction was monitored by TLC (50% ether in hexane). After 4 hours and 10 minutes, the reaction was cooled. The reaction was extracted with ether and washed one time each with water, saturated sodium bicarbonate, and brine. The organic layer dried over magnesium sulfate, filtered, and concentrated. The compound was chromatographed on silica gel, eluting with ether. The desired product, compound Ia, was obtained in 68% yield (1.18 g).

Example 2

Preparation of 1,2-O-Isopropylidene-3-O-decyl-6-deoxy-6-N-(1,2,3,4-tetrahydroisoquinolinyl)-α,D-glucofuranose (IIa)

1,2-O-Isopropylidene-3-O-decyl-6-O-tosyl-α,D-glucofuranose (2.3 g) was combined with tetrahydroisoquinoline (6 mL) in a round bottom flask, and stirred at 73–75° C. The reaction was monitored by TLC (50% ether in hexane). After 1.5 hours, the reaction was cooled. The reaction was extracted with ether and washed three times each with water, saturated sodium bicarbonate, and brine. The organic layer was dried over magnesium sulfate, filtered, and concentrated. The compound was chromatographed on silica gel, eluting with ether. Compound IIa was obtained in 61% yield (1.3 g).

Example 3

Preparation of 1,2-O-Isopropylidene-3-O-decyl-6-deoxy-6-N-{[(3,4-difluorophenyl)methyl]amino}-α,D-glucofuranose (IIb)

1,2-O-Isopropylidene-3-O-decyl-6-deoxy-6-O-tosyl-α,D-glucofuranose (2.0 g) was combined with 3,4-(difluoro)-benzylamine (5 g) in a round bottom flask and stirred at 69–70° C. The reaction was monitored by TLC (50% ether in hexane). After 6 hours the reaction was cooled. Water was added to the reaction and the mixture extracted with ether. The organic layer was then washed three times each with water, saturated sodium bicarbonate, and brine. The organic layer was dried over magnesium sulfate, filtered, and concentrated. The compound was chromatographed on silica gel, eluting with 50% ether in hexane. Compound IIb was obtained in 64% yield (1.2 g).

Example 4

Preparation of 1,2-O-Isopropylidene-3-O-heptyl-6-deoxy-6-N-{[2-fluorophenyl)methyl]amino}-α,D-glucofuranose (IIc)

Preparation of 1,2:5,6-Di-O-Isopropylidene-3-O-heptyl-α,D-glucofuranose 1.2:5,6-Di-O-Isopropylidene-α,D-glucofuranose (75.3 g), 0.290 mol) was combined with dried, crushed sodium hydroxide, (34.3 g, 0.86 mol), and heptylbromide, (62.6 g, 0.345 mol), in a round bottom flask. The reaction was heated with stirring and monitored by TLC (50% ether in hexane). After 6 hours at 100–130° C., and 16 hours at ambient temperature, the reaction was extracted with ether and filtered. The compound was chromatographed on silica gel, eluting with 10% ether in hexane. The title compound was obtained in 83% yield (86 g).

Preparation of 1,2-O-Isopropylidene-3-O-heptyl-α, D-glucofuranose 1,2;5,6-Di-O-isopropylidine-3-O-heptyl-α,D-glucofuranose (86 g) was dissolved in tetrahydofuran (86 mL) and cooled to 0–5° C. with stirring. Perchloric acid (86 mL, 30% vol.) was then added drop-wise at a rate of 1 drop/sec (23 minute addition time). Reaction was monitored by TLC (50% ether in hexane). After 10 minutes at 0–5° C. and 16.5 hours at −20° C., the reaction was neutralized to pH 7–8 by drop-wise addition of saturated potassium carbonate solution. The reaction was filtered, and the tetrahydrofuran evaporated. The residue was dissolved in ether and any water present was removed by separatory funnel and magnesium sulfate. The organic layer was filtered and concentrated. The compound was chromatographed on silica gel, eluting with 20% ether in hexane to ether. The desired compound was obtained in 69% yield (52.7 g).

Preparation of 1,2-O-Isopropylidene-3-O-heptyl-6-O-tosyl-α,D-glucofuranose 1,2-O-Isopropylidene-3-O-heptyl-α,D-glucofuranose (25.4 g, 0.0799 mol) was dissolved in pyridine (50 mL) and stirred in a round bottom flask equipped with a drying tube at 0–5° C. Tosyl chloride (13.32 g, 0.0699 mol) was dissolved in pyridine (20 mL) and added drop-wise to the reaction at a rate of 1 drop/sec. The reaction was monitored by TLC (50% ether in hexane). After 2 hours at 0–5° C. and 15 hours at −20° C., and 5 hours at 0–5° C., the reaction was poured into ice water and extracted with ether. The organic layer was washed three times each with water, saturated sodium bicarbonate, and brine. The organic layer was dried over magnesium sulfate, filtered, and concentrated. The compound was chromatographed on silica gel, eluting with 10% ether to 40% ether in hexane. The desired tosylate was obtained in 87% yield (25.6 g).

Preparation of 1,2-O-Isopropylidene-3-O-heptyl-6-deoxy-6-N-[[(2-fluoropheny)methyl]amino]-α,D-glucofuranose (IIc)

1,2-O-Isopropylidene-3-O-heptyl-6-O-tosyl-α,D-glucofuranose (3.4 g) was combined with 2-fluorobenzylamine (9 mL) in a round bottom flask. The reaction was stirred at 75° C. and monitored by TLC (70% ether in hexane). After 5 hours the reaction was cooled. The reaction was extracted with ether and washed three times each with water, saturated sodium bicarbonate and brine. The organic layer was dried over magnesium sulfate, filtered, and concentrated. The compound was chromatographed on silica gel, eluting with 50% ether in hexane. Compound IIc was obtained in 48% yield (1.47 g).

Example 5

Preparation of 1,2-O-Isopropylidene-3-O-heptyl-6-deoxy-6-N-[(2-pyridinylmethyl)amino]-α,D-glucofuranose (IId)

1,2-O-Isopropylidene-3-O-heptyl-6-O-tosyl-α,D-glucofuranose (1.5 g) was combined was 2-(aminomethyl)-pyridine (3 mL) in a round bottom flask with stirring. The reaction was heated to 75–80° C. and monitored by TLC (ether/ammonium hydroxide). After 2 hours, the reaction was dried under high vacuum to remove excess amine. The residue was dissolved in ether and washed once each with water, saturated sodium bicarbonate and brine. The organic layer was dried over magnesium sulfate, filtered and concentrated. The compound was chromatographed on silica gel, eluting with ether to 5% MeOH in ether. Compound IId was obtained in 69% yield (0.9 g).

Example 6

Preparation of 1,2-O-Isopropylidene-3-O-heptyl-6-deoxy-6-N-[(2-pyridinylmethyl)amino]-α,D-glucofuranose hydrochloride salt (IIe)

1,2-O-Isopropylidene-3-O-heptyl-6-deoxy-6-N-[(2-pyridinylmethyl)amino]-α,D-glucofuranose (4 g) was dissolved in acetone (75 mL). Hydrochloric acid (3N) was added drop-wise until solution became acidic. Ether (100 mL) was added and the solution was cooled. The resulting crystals were filtered and washed with cooled ether. Compound IIe was obtained in 53% yield (2.3 g).

Example 7

Preparation of 1,2-O-Isopropylidene-3-O-cyclohexylmethyl-6-deoxy-6-N-[(4-pyridinylmethyl)amino]-α,D-glucofuranose (IIf)

Preparation of 1,2:5,6-Di-O-isopropylidene-3-O-cyclohexylmethyl-α,D-glucofuranose 1,2:5,6-Di-O-isopropylidene-α,D-glucofuranose (5.05 g, 0.0194 mol) was combined with crushed, dried sodium hydroxide (2.8 g, 0.0700 mol) and cyclohexylmethylbromide (4.09 g, 0.0231 mol) in a round bottom flask. The reaction was stirred at 140° C. for 3.5 hours, left at −20° C. for 15 hours, and stirred at 140° C. for one hour. The reaction was monitored by TLC (70% ether in hexane). The reaction was cooled, extracted with ether, and filtered. The compound was chromatographed on silica gel, eluting with 10% ether in hexane. The desired product was obtained in 80% yield (3.4 g). Some cyclohexylmethylbromide remained but the compound was usable in further synthesis.

Preparation of 1,2-O-Isopropylidene-3-O-cyclohexylmethyl-α,D-glucofuranose 1,2:5,6-Di-O-isopropylidene-3-O-cyclohexylmethyl-α,D-glucofuranose (43 g) was dissolved in tetrahydofuran (45 mL) and cooled to 0–5° C. with stirring. Perchloric acid (45 mL, 30% vol) was added drop-wise to the solution at a rate of 1 drop/second (16 minute addition time). Reaction was monitored by TLC (ether). After 35 minutes, the reaction was quenched by drop-wise addition of potassium carbonate (saturated solution). The reaction was diluted with tetrahydrofuran. When the pH of the reaction reached 7–8, the mixture was filtered and the tetrahydrofuran was evaporated. The residue was dissolved in ether and water removed by separatory funnel and magnesium sulfate. The organic layer was filtered and concentrated. The compound was chromatographed on silica gel, eluting with 50% ether/hexane. The desired product was obtained in 55% yield (21 g).

Preparation of 1,2-O-Isopropylidene-3-O-cyclohexylmethyl-6-O-tosyl-α,D-glucofuranose 1,2-O-Isopropylidene-3-O-cyclohexylmethyl-α,D-glucofuranose (21.0 g, 66.4 mmol) was dissolved in pyridine (30 mL) in a round bottom flask equipped with a drying tube, and cooled to 0–5° C. with stirring. Tosyl chloride (12.7 g, 0.0664 mol) was dissolved in pyridine (20 mL) and added drop-wise to the reaction at a rate of 1 drop/sec.(30 minute addition time). The reaction was monitored by TLC (70% ether in hexane). After 3 hours the reaction was poured into ice water and extracted with ether. The organic layer was washed three times each with water, saturated sodium bicarbonate, and brine. The organic layer was dried over magnesium sulfate, filtered and concentrated. The compound was chromatographed on silica gel, eluting with 30% ether in hexane. The title compound was obtained in 67% yield (20.8 g).

Preparation of 1,2-O-Isopropylidene-3-O-cyclohexylmethyl-6-deoxy-6-N-[(4-pyridinylmethyl)amino]-α,D-glucofuranose (IIf)

1,2-O-Isopropylidene-3-O-cyclohexylmethyl-6-O-tosyl-α,D-glucofuranose (2.3 g) was combined with 4-(pyridinylmethyl)amine (8 mL) in a round bottom flask. The reaction was stirred at 75° C. and monitored by TLC (70% ether in hexane). After 3 hours the reaction was cooled and extracted with ether. The mixture was washed one one time each with water, saturated sodium bicarbonate, and brine. The organic layer was dried over magnesium sulfate, filtered, and concentrated. The compound was chromatographed on silica gel, eluting with ether to 5% MeOH in ether. Compound IIf was obtained in 55% yield (1.1 g).

Example 8

Preparation of 1,2-O-Isopropylidene-3-O-cyclohexylmethyl-6-deoxy-6-N-{[3-methoxyphenyl methyl]amino}-α,D-glucofuranose (IIg)

1,2-O-Isopropylidene-3-O-cyclohexylmethyl-6-O-tosyl-α,D-glucofuranose (1.9 g) was combined with 3-methoxybenzylamine (7 mL) in a round bottom flask. The reaction was stirred at 75° C. and monitored by TLC (ether/ammonium hydroxide). After 1.5 hours, the reaction was cooled and extracted with ether. The mixture was washed three times each with water, saturated sodium bicarbonate and brine. The organic layer was dried over magnesium sulfate, filtered and concentrated. The compound was chromatographed on silica gel, eluting with ether. Compound IIg was obtained in 34% yield (0.6 g).

Example 9

Preparation of 1,2-O-Isopropylidene-3-O-cyclohexylmethyl-6-deoxy-6-N-{[3-(N-imidazolyl)propyl]amino}-α,D-glucofuranose (IIh)

1,2-O-Isopropylidene-3-O-cyclohexylmethyl-6-O-tosyl-α,D-glucofuranose (2.3 g) was combined with N-(3-aminopropyl) imidazole (7 mL) in a round bottom flask. The reaction was stirred at 75° C. and monitored by TLC (50% ether in hexane). After 1 hour 43 minutes, the reaction was cooled. The crude reaction mixture was chromatographed on silica gel, eluting with ether to 5% MeOH in ether. Compound IIh was obtained in 7% yield (0.15 g).

Example 10

Preparation of 1,2-O-Isopropylidene-3-O-n-heptyl-6-deoxy-6-N-(4-pyridinylamino)-α,D-glucofuranose (IIkkk)

1,2-Isopropylidene-3-O-n-heptyl-6-O-tosyl-α,D-glucofuranose (6.65 g) was dissolved in p-dioxane (9 mL) and to this was added 4-aminopyridine (5.09 g). The reaction mixture was heated to 110° C. for five hours then cooled to room temperature, concentrated under high vacuum and the residue obtained extracted with diethyl ether (4×50 ml). The combined ether extracts were washed with saturated sodium bicarbonate, dried (MgSO$_4$), filtered and concentrated. The crude reaction mixture was chromatographed on silica gel (90:10:0.1 chloroform/methanol/triethylamine) to give 1,2-O-Isopropylidene-3-O-n-heptyl-6-deoxy-6-N-(4-pyridinylamino)-α,D-glucofuranose (0.9 g).

Example 11

Preparation of 1,2-O-Isopropylidene-3-O-cyclohexylmethyl-6-deoxy-6-N-[(1-naphthylmethyl)amino-α,D-goucofuranose (IIuu)

1,2-O-Isopropylidene-3-O-cyclohexylmethyl-6-O-tosyl-α,D-glucofuranose (2.0 g) was combined with 1-aminomethyl naphthylene (8 mL) in a round bottom flask. The reaction mixture was heated, with stirring, at 70° C. for 5 hours, cooled and chromatographed on silica gel (1:1 diethyl ether/hexane) to give 1,2-O-Isopropylidene-3-O-cyclohexylmethyl-6-deoxy-6-N-[(1-naphthylmethyl)amino-α,D-glucofuranose (1.32 g).

Example 12

Mouse Arachidonic Acid Ear Assay

To assess potential anti-inflammatory activity of compound IIe, a standard Mouse Arachidonic Acid Ear assay was performed. This assay tests the ability of a specific compound to antagonize an inflammatory response.
Specific Method
Compound IIe was applied topically to one ear of 3 Balb/CByJ mice at a concentration of 2 mg/10 μl. After 30 minutes, arachidonic acid was applied to both ears of each mouse. One half hour later, the mice were sacrificed and an 8 mm diameter section of each ear was weighed. The weights of the compound treated and untreated ears were compared as a measure of the anti-inflammatory properties of the compound. Results are expressed using a simple qualitative scoring system in which 0=inactive, 1+=slightly active, 2+=moderately active and 3+=highly active.
Results
The (highly active) anti-inflammatory effects of compound IIe were scored as 3+ based on the results of this assay.

Example 13

Ex Vivo Mixed Lymphocyte Response (MLR) Assay

The potential immunomodulatory effects of compound IIe were studied in an ex vivo Mixed Lymphocyte Response (MLR) assay system. This assay tests the ability of a specific compound to regulate a cell mediated immune response involving lymphocyte cell activation and proliferation.
Specific Method
Balb/cJ mice were dosed orally for 7 days with 5, 10 or 25 mg/kg of compound IIe, with water only as the vehicle control or with 50 mg/kg of cyclophosphamide as the positive control. Dose groups consisted of 10 mice per group. At the end of the dosing period, mice were euthanized by cervical dislocation and their spleens were removed. Single cell suspensions of each spleen were prepared in culture medium (DMEM supplemented with 10% calf serum, 2 Mm glutamine, 500 units penicillin/streptomycin, and $4 \times 10^{-5}$ M 2-mercaptoethanol, sodium pyruvate, non-essential amino acids, essential amino acids, nucleic acids, and MEM vitamins) using a Teflon pestle. The cells were centrifuged at 1500 RPM and the pellets resuspended in ACT (0.15 M Tris, 0.14 M Ammonium Chloride, pH 7.2) in order to lyse the red blood cells. After a five minute incubation in a 37° C. waterbath, the cells were washed and resuspended in culture medium.

The splenic lymphocytes were counted using an electronic Coulter Counter. Spleen cells from C57BL/6 mice were used as stimulator cells and were prepared in the same way. The stimulator cells were then treated with 100 µg/mL of mitomycin for 20 minutes at 37° C., then washed five times in culture medium. The proliferative response was measured by culturing $\times 10^5$ responder spleen cells with $5 \times 10^5$ stimulator cells in 96-well microliter plates.

Syngeneic control cultures using mitomycin C treated spleen cells from normal BALB/c mice as the stimulator cells were run also. All cultures were run in triplicate. After incubation for 5 days at 37° C. with 5% $CO_2$, the amount of cell proliferation was measured by adding 20 µl of MTT (3-[4,5-dimethylthiazol-2-yl)-2,5-diphenyl-tetrazolium bromide](10 mg/mL in PBS) to each well. Plates were incubated for 4 hours at 37° C., after which 180 µl of supernatant were removed and 180 µl of 10% SDS in PBS were added. After an overnight incubation, the optical density (OD) of each well was read on a Molecular Devices microplate reader at 570–650 nm.

The result for each mouse was determined by calculating the difference between the allogeneic cultures and the syngeneic cultures for each spleen cell population. The mean of the test article group was determined and compared to the mean of the control group.

Statistical analyses were made in Systat (version 4.0, Systat, Inc.). The Tukey multiple comparisons test was used to make pairwise comparisons between groups to detect statistically significant differences.

Results

The results of this study are presented in Table 1. Statistically significant inhibition of mixed lymphocyte responsiveness in treated mice was achieved at all doses of compound IIe.

TABLE 1

Effect of Compound IIe on a Mixed Lymphocyte Response (MLR) Assay in Mice

| Group | Treatment | Dose (mg/kg) | Difference (mean ± SD) | % Change[1] | P Value[2] |
|---|---|---|---|---|---|
| 1 | Vehicle | — | 1.057 ± 0.554 | — | — |
| 2 | Compound IIe | 5 | −0.022 ± 0.935 | −102 | 0.009* |
| 3 | Compound IIe | 10 | −0.135 ± 0.489 | −113 | 0.004* |
| 4 | Compound IIe | 25 | 0.108 ± 0.620 | −90 | 0.028* |
| 5 | Cyclophosphamide | 50 | −0.665 ± 0.735 | −163 | <0.001* |

[1]% change from the vehicle control
[2]Comparison to the vehicle control
*Statistically significant Example 14

Ex Vivo Macrophage Phagocytosis Assay

The potential immunomodulatory effects of compound IIe were studied in an ex vivo Macrophage Phagocytosis Assay system. Macrophage phagocytic activity is involved in antigen presentation and accessory cell function of macrophages, which are functions critical to cell mediated immunity.

Specific Method

Balb/cByJ mice were dosed orally for 7 days with 5, 10 or 25 mg/kg of compound IIe or with water only as the vehicle control. Dose groups consisted of 10 mice per group. At the end of the dosing period, mice were euthanized by decapitation. The peritoneal macrophages were collected by injecting 5 mL of culture medium (RPMI-1640 with Hepes, supplemented with 10% fetal calf serum (FCS), 2 mM glutamine, and 500 units penicillin/streptomycin) into the peritoneal cavity of each mouse and collecting the wash.

The cells were centrifuged at 1500 rpm for 5 minutes and resuspended in 2 mL of culture medium. 12 µL of latex particles were added to each tube. Tubes were rotated overnight at 37° C. After incubation, the cells were underlaid with 2 mL of fetal calf serum and centrifuged at 1500 rpm for 10 minutes to form pellets. The pellets were resuspended in medium and again underlaid with serum and spun. The pellets were resuspended in 0.5 mL of medium, at least 200 viable cells were counted and the number of cells containing latex beads (phagocytic cells) was determined. The percent of phagocytic cells was determined.

The means for each group were determined. The percent phagocytic cells obtained from the test article treated group was compared to that obtained from the negative control treated group and the percent of control was calculated.

Statistical analyses were made in Systat (version 4.0, Systat, Inc.). The Tukey multiple comparisons test was used to make pairwise comparisons between groups to detect statistically significant differences.

Results

The results of this study are presented in Table 2. Increased phagocytic activity of macrophages from compound IIe treated mice was observed of all dose levels, with statistically significant increases observed in cultures from the 10 mg/kg dose group.

TABLE 2

Effect of Compound IIe on Macrophage Phagocytosis in Mice

| Group | Treatment | Dose (mg/kg) | % Phagocytic cells (mean ± SD) | % Change[1] | P Value[2] |
|---|---|---|---|---|---|
| 1 | Vehicle | — | 9.990 ± 2.976 | — | — |
| 2 | Compound IIe | 5 | 15.489 ± 5.590 | 55 | 0.136 |
| 3 | Compound IIe | 10 | 19.220 ± 7.533 | 92 | 0.003* |
| 4 | Compound IIe | 25 | 13.740 ± 4.350 | 38 | 0.414 |

[1]% change from the vehicle control
[2]Comparison to the vehicle control
*Statistically significant Example 15

In Vitro Cytotoxicity Screening

Compounds of the present invention were screened in in vitro cytotoxicity screens to determine appropriate non-toxic levels for testing in activity screens.

Specific Method

A mouse macrophage cell line (P388D1) was used at mid-log phase growth to evaluate in vitro cytotoxicity. Varying dilutions of compound were prepared from stock solutions consisting of compound dissolved in DMSO at 100 mg/mL. Compound dilutions were added to $2 \times 10^5$ cells/well in 96 well microtitre plates. After 24 hours of incubation at 37° C. and 5% $CO_2$, the viability of cells in each well was determined by trypan blue exclusion analysis. The effects of each compound on cellular viability were determined using the following formula:

% viable unknown/% of viable control=% viability.

Results

A compound was considered cytotoxic if less than 70% viability was observed. The following compounds were found to be cytotoxic at an in vitro concentration of 1–10 μg/mL and were not subjected to a comprehensive testing regimen: IIi, IIj, IIt, IIv, IIw, IIy, IIaa, IIcc, IIdd, IIee.

Example 16

In Vitro Concanavalin A (Con A) Stimulated T Lymphocyte Proliferation Assay

Compounds of the invention were tested for inhibitory effects on T lymphocyte activation and proliferation in an in vitro Concanavalin A (Con A) Stimulated T Lymphocyte Proliferation Assay.

Specific Method

Balb/cByJ mice were euthanized by cervical dislocation and their spleens were removed aseptically. Single cell splenic lymphocyte suspensions were prepared in buffered Earles Balanced Salt Solution (EBSS). Erythrocytes were removed by water lysis and spleen cells were resuspended in complete media (CM) consisting of RPMI 1640 media supplemented with 10% fetal calf serum, 1 mM Hepes buffer, 1 mM L-glutamine, 100 U Penicillin/Streptomycin and $5 \times 10^{-5}$ M 2-mercaptoethanol. $2 \times 10^5$ spleen cells per well were incubated in 96 well microtitre plates with several concentrations of compound or with media only as the positive control. Triplicate cultures were run for each compound dose as well as for control wells. Compounds were prepared in dimethylsulfoxide (DMSO) at stock concentrations of 100 mg/mL and dilutions were prepared in CM. 5 μg/well of Con A (a T cell mitogen) was added to each well. Cultures were incubated for 24 hours at 37° C. and 5% $CO_2$. Potential cytotoxic effects of the compounds was predetermined by trypan blue exclusion viability testing of mouse cells exposed to varying concentrations of the specific compounds as described in Example 15. Only non-cytotoxic concentrations of compounds were tested. At the end of the incubation period, cellular proliferation was determined using a commercially available MTT kit (Promega G4000). The optical density (OD) of each well was read on a Molecular Devices microplate reader at 570–650 nm. Results are expressed as percent change from control which is determined using the following formula:

(OD unknown−OD control)/OD control×100=% change

Results

The potent inhibitory effects of compounds of formula I on mitogen induced T lymphocyte proliferation and activation are presented in Table 3. The potent inhibitory effects of compounds of formula II are shown in Tables 4A and 4B. A compound is considered active in the Con A stimulated T lymphocyte proliferation assay if a greater than −20% inhibition of the control proliferative response is achieved at a concentration within the 0.00001–10 μg/mL of compound dose range.

TABLE 3

Inhibition of Con A Stimulated* T Lymphocyte Proliferation

| | in vitro concentration of compound (μg/mL) | | | | |
|---|---|---|---|---|---|
| Compound | 10 | 1 | 0.1 | 0.01 | 0.001 |
| Ib | −97 | −23 | −18 | −20 | −13 |
| Ia | −99 | −15 | −15 | −19 | −12 |

*Results expressed as % change from control; nt = not tested

TABLE 4A

Inhibition of Con A Stimulated* T Lymphocyte Proliferation

| | in vitro concentration of compound (μg/mL) | | | | | | |
|---|---|---|---|---|---|---|---|
| Compound | 10 | 1 | 0.1 | 0.01 | 0.001 | 0.0001 | 0.00001 |
| IIaa | nt | −34 | −23 | −20 | −17 | nt | nt |
| IIg | 0 | −10 | −14 | −28 | −34 | −42 | −48 |
| IIgg | −95 | −9 | −15 | −23 | −20 | nt | nt |
| IIh | −19 | −19 | −31 | −21 | −23 | nt | nt |
| IIa | −91 | −12 | −28 | −28 | −27 | nt | nt |
| IIii | −100 | −17 | −27 | −26 | −29 | nt | nt |
| IIjj | −96 | −211 | −38 | −55 | 34 | −3 | nt |
| IIkk | −96 | −16 | −17 | −24 | −13 | nt | nt |
| IIll | −91 | −22 | −17 | −20 | −14 | nt | nt |
| IIk | −62 | −12 | −15 | −21 | −11 | nt | nt |
| IIl | −100 | −12 | −4 | nt | nt | nt | nt |
| IIn | −32 | −21 | −20 | −21 | −21 | nt | nt |
| IIq | −20 | −29 | −26 | −18 | −20 | nt | nt |
| IIr | −99 | −12 | 6 | nt | nt | nt | nt |
| IIs | −60 | −10 | 5 | nt | nt | nt | nt |
| IIx | nt | −10 | 4 | 0 | nt | nt | nt |
| IImm | −19 | −27 | −27 | −21 | −13 | nt | nt |
| IInn | −18 | −29 | −36 | −27 | −12 | nt | nt |
| IIb | −21 | −22 | −29 | −20 | −10 | nt | nt |

*Results expressed as % change from control; nt = not tested.

TABLE 4B

Inhibition of Con A Stimulated* T Lymphocyte Proliferation

| | | in vitro concentration of compound (μg/mL) | | | | | |
|---|---|---|---|---|---|---|---|
| Compound | | 100 | 50 | 10 | 1 | 0.1 | 0.01 | 0.001 |
| IIoo | 93592 | nt | nt | −21 | 28 | 29 | 24 | 5 |
| IIss | 93598 | nt | nt | −30 | 23 | 14 | 9 | 9 |
| IIvv | 93605 | −86 | 5 | 40 | 42 | 35 | 38 | 13 |
| IIww | 93606 | nt | −99 | 24 | 26 | 29 | 25 | 8 |
| IIxx | 93607 | nt | nt | −31 | 13 | 19 | 1 | −4 |
| IIaaa | 93618 | nt | nt | −92 | 14 | 11 | 17 | 6 |
| IIddd | 93621 | nt | −73 | 5 | 8 | 5 | 8 | 17 |
| IIfff | 93623 | nt | nt | −33 | 11 | 2 | 4 | −3 |
| IIlll | 93635 | −97 | −54 | 23 | 26 | 21 | 30 | 23 |
| IInnn | 93646 | nt | nt | −96 | 5 | 8 | 9 | 3 |
| IIsss | 93515 | nt | nt | nt | −24 | −16 | −22 | −16 |

*Results expressed as % change from control; nt = not tested.

Example 17

In vitro Mixed Lymphocyte Response (MLR) Assay

The potential immunomodulatory effects of compounds of the invention were studied in an in vitro MLR assay system. This assay tests the ability of a specific compound to regulate a cell mediated immune response involving T lymphocyte activation and proliferation.

Specific Method

Balb/cByJ (responder) and C57B1/6 (stimulator) mice were euthanized by cervical dislocation and their spleens were removed aseptically. Single cell splenic lymphocyte suspensions were prepared as described in Example 16. The C57B1/6 cells were used as the stimulator cell type and were treated with mitomycin c to prevent proliferative activity. The proliferative response of responder cells to stimulator cells was measured by incubating $5 \times 10^5$ of each cell type per well together along with media alone (control) or with varying non-toxic concentrations of compound in 96 well microtitre plates.

Compound cytotoxicity was monitored as described in Example 15. Triplicate cultures were run for each compound dose and for control wells. Compounds were prepared as described in Example 16 and were added to the appropriate test wells. After 5 days incubation at 37° C. and 5% $CO_2$, each well was pulsed overnight with $2\mu Ci$ of $^3H$-thymidine and harvested the next day on a PHD cell harvester. Cellular incorporation of $^3H$-thymidine (cpm) was determined with a Packard scintillation counter. Results are expressed as percent change from control MLR's and are calculated using the following formula:

$$\frac{(cpm\ unknown\ MLR - cpm\ control\ MLR)}{cpm\ control\ MLR} \times 100 = \%\ change$$

Results

The potent inhibitory effects of compounds of formula I on in vitro mixed lymphocyte responsiveness are presented in Table 5. The potent inhibitory effects of compounds of formula II are presented in Table 6. A compound is considered active in the in vitro Mixed Lymphocyte Response Inhibition assay when greater than −30% inhibition of the control response is mediated at the 0.0001–10 μg/mL concentration range of compound.

TABLE 5

Mixed Lymphocyte Response Inhibition* in vitro concentration of compound (μg/mL)

| Compound | 10 | 1 | 0.1 | 0.01 | 0.001 | 0.0001 |
|---|---|---|---|---|---|---|
| Ib | −100 | −52 | −60 | −39 | −1 | −16 |
| Ia | −195 | −112 | −140 | −47 | −58 | nt |

*Results expressed as % change from control; nt = not tested

TABLE 6

Mixed Lymphocyte Response Inhibition* in vitro concentration of compound (μg/mL)

| Compound | 10 | 1 | 0.1 | 0.01 | 0.001 | 0.0001 |
|---|---|---|---|---|---|---|
| IIe | nt | −63 | −53 | −42 | −52 | −55 |
| IIz | −7 | −27 | −50 | −51 | −5 | −78 |
| IIbb | −100 | −62 | −85 | 51 | −19 | −21 |
| IIc | −100 | −34 | 0.5 | −35 | −21 | 43 |
| IIf | −88 | −14 | −66 | −8.7 | −59 | −14 |
| IIg | −76 | −92 | −83 | −60 | −64 | 34 |
| IIgg | −100 | −100 | −90 | −83 | −86 | −30 |
| IIhh | −55 | −84 | −75 | −41 | −45 | 21 |
| IIh | −100 | −63 | −51 | −91 | −6 | 22 |

TABLE 6-continued

Mixed Lymphocyte Response Inhibition* in vitro concentration of compound (μg/mL)

| Compound | 10 | 1 | 0.1 | 0.01 | 0.001 | 0.0001 |
|---|---|---|---|---|---|---|
| IIa | −100 | −67 | −83 | −63 | 44 | 27 |
| IIii | −100 | −52 | −49 | −58 | −0.1 | 37 |
| IIjj | −96 | −21 | −38 | −55 | 34 | −3 |
| IIkk | −100 | −100 | −38 | −67 | 2 | −1 |
| IIll | −100 | −71 | 2 | −10 | 28 | 0.3 |
| IIp | nt | −36 | −35 | 50 | 94 | nt |
| IIs | −100 | −70 | −15 | −8 | −7 | 46 |
| IIu | −100 | −65 | 93 | 23 | 74 | nt |
| IIx | nt | −28 | −40 | 53 | 49 | 22 |
| IIrrr | nt | −45 | −43 | −60 | −31 | nt |
| IIqqq | nt | −77 | −65 | −64 | −43 | nt |
| IIooo | −58 | −72 | −49 | −65 | −43 | nt |
| IIppp | nt | −28 | −33 | −83 | −71 | nt |
| IIsss | nt | −34 | 122 | −25 | 100 | nt |

*Results expressed as % change from control; nt = not tested

Example 18

In Vitro Mixed Lymphocyte Response (MLR) Assay Alternate Specific Method Used for Formula II Compounds Specific Method C5B1/6 (responder) and Balb/cByJ (stimulator) mice were euthanized by cervical dislocation and their spleens were removed aseptically. Single cell splenic lymphocyte suspensions were prepared as described in Example 14.

The Balb/cByJ cells were used as the stimulator cell type and were treated with mitomycin c to prevent proliferative activity. The proliferative response of the responder cells to stimulator cells was measured by incubating $4 \times 10^5$ of each cell type per well together along with media alone [control] or with varying non-toxic concentrations of compound in 96 well mitrotitre plates.

The remainder of the assay and data analyses were performed as described in Example 17. The results are shown in Table 7.

TABLE 7

Mixed Lymphocyte Response Inhibition* in vitro concentration of compound (μg/mL)

| Compound | 100 | 50 | 10 | 1 | 0.1 | 0.01 | 0.001 |
|---|---|---|---|---|---|---|---|
| IIoo | nt | nt | −84 | −2 | 35 | 36 | 18 |
| IIpp | nt | nt | nt | 41 | 11 | −29 | −13 |
| IIqq | nt | nt | −89 | −5 | −4 | −12 | 7 |
| IIrr | nt | nt | −103 | −16 | −24 | −2 | −4 |
| IIss | nt | nt | −94 | −21 | 4 | −21 | −4 |
| IItt | nt | nt | −42 | −34 | 15 | 22 | 5 |
| IIuu | nt | nt | nt | −7 | −30 | −23 | −4 |
| IIvv | nt | nt | −1 | −7 | 2 | −22 | −34 |
| IIww | nt | −103 | 255 | −6 | 7 | −3 | −33 |
| IIxx | nt | nt | −96 | 15 | 5 | 13 | −25 |
| IIyy | nt | −67 | −24 | 5 | −4 | 13 | 16 |
| IIzz | nt | nt | −88 | −21 | −30 | −31 | −19 |
| IIaaa | nt | nt | −104 | −10 | −43 | −22 | −30 |
| IIbbb | nt | −38 | −102 | −33 | −44 | −37 | −28 |
| IIccc | nt | nt | −98 | −27 | −32 | −5 | −26 |
| IIddd | nt | −104 | −88 | −5 | −32 | −34 | −27 |
| IIeee | nt | nt | −99 | −18 | −41 | −21 | −25 |
| IIfff | nt | nt | −104 | −46 | −52 | −44 | −32 |
| IIggg | nt | −104 | −42 | −53 | −34 | −23 | −35 |

TABLE 7-continued

Mixed Lymphocyte Response Inhibition* in vitro concentration of compound (µg/mL)

| Compound | 100 | 50 | 10 | 1 | 0.1 | 0.01 | 0.001 |
|---|---|---|---|---|---|---|---|
| IIhhh | nt | nt | nt | −27 | −26 | −27 | −45 |
| IIiii | nt | nt | −66 | −32 | −4 | −25 | −35 |
| IIjjj | nt | nt | −90 | −21 | −36 | −27 | −24 |
| IIkkk | nt | nt | 28 | 2 | 6 | −3 | −33 |
| IIlll | −104 | −104 | −40 | −28 | −34 | −36 | −12 |
| IImmm | nt | nt | −96 | −22 | −31 | −34 | −34 |
| IInnn | nt | nt | nt | −10 | −35 | −42 | −33 |

*Results expressed as % change from control;
nt—not tested

We claim:

1. A 5,6-dideoxy, 5-amino derivative of idose of the formula (I):

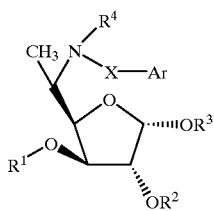

(I)

wherein
  $R^1$ is a $C_3$ to $C_{15}$ branched or unbranched alkyl group, or a $(C_1-C_3)$-alkyl-$(C_3-C_7)$-cycloalkyl $R^2$ and $R^3$ together with the atoms carrying them form an actual protecting group;
  Ar is a substituted or unsubstituted, aromatic or heteroaromatic group selected from the group consisting of imidzaolyl, furanyl, pyrrolyl, 1,3-benzodioxol-5-ylmethyl, pyridinyl, thienyl, naphthyl, and phenyl;
  $R^4$ is hydrogen or a branched or unbranched lower alkyl group having 1 to 5 carbon atoms; and
  X is a bond joining N and Ar or a branched or unbranched lower alkyl group having 1 to 5 carbon atoms, or together with $R^4$, and the nitrogen carrying them, forms a 5-, 6-, or 7-membered heterocycle fused to said aromatic or heteroaromatic group Ar;
  or a physiologically acceptable salt thereof.

2. A 5,6-dideoxy, 5-amino derivative of idose of claim 1, wherein $R^1$ is a $C_4$ to $C_{12}$ unbranched alkyl group, a cyclopropylmethyl group, a cyclohexylmethyl group or a cyclohexylpropyl group; $R^2$ and $R^3$ together with the atoms carrying them form an acetal protecting group selected from the group consisting of an isopropylidene and a cyclohexylidene group; Ar is a substituted or unsubstituted, aromatic or heteroaromatic group selected from the group consisting of furanyl, thienyl, pyridinyl, napthyl and a phenyl group of the formula:

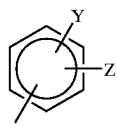

Y and Z are each independently H, F, Cl, Br, $OCH_3$, CN, $NO_2$, $CF_3$, $OCF_3$ or NR'R", wherein R' and R", which may be the same or different, are a branched or non-branched, substituted or non-substituted alkyl group;
  $R^4$ is hydrogen, or a methyl, ethyl or propyl group; and
  X is a bond or a branched or unbranched alkyl group having 1 to 5 carbon atoms, or together with $R^4$, and the nitrogen carrying them, form a hydrogenated isoquinoline group; or a physiologically acceptable salt thereof.

3. The 5,6-dideoxy, 5-amino derivative of idose of claim 2, 1,2-O-isopropylidene-3-O-decyl-5,6-dideoxy-5-N-[(2-pyridinylmethyl)amino]-β,L-idofuranose, or a physiologically acceptable salt thereof.

4. The 5,6-dideoxy, 5-amino derivative of idose of claim 2, 1,2-O-isopropylidene-3-O-decyl-5,6-dideoxy-5-N-[(2furanylmethyl)amino]-β,L-idofuranose, or a physiologically acceptable salt thereof.

5. The 5,6-dideoxy, 5-amino derivative of idose of claim 2, 1,2-O-isopropylidene-3-O-decyl-5,6-dideoxy-5-N-[[2-(2-pyridinyl)ethyl]amino]-β,L-idofuranose, or a physiologically acceptable salt thereof.

6. A pharmaceutical composition for the treatment of an inflammatory and/or autoimmune disorder comprising an effective amount of a compound according to claim 1, or a physiologically acceptable salt thereof, and a pharmaceutically acceptable carrier.

7. A method of treating an animal or human suffering from an inflammatory and/or autoimmune disorder comprising administering thereto the compound according to claim 1, or physiologically acceptable salt thereof, in an amount effective to treat an inflammatory and/or autoimmune disorder.

8. A method of claim 7, wherein the inflammatory and/or autoimmune disorder treated is rheumatoid arthritis, psoriasis, psoriatic arthritis, scleroderma, systemic lupus erythematosus, multiple sclerosis, inflammatory bowel disease, osteoarthritis, or asthma.

9. A 6-deoxy, 6-amino derivative of glucose of the formula (II):

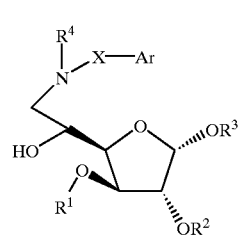

(II)

wherein
  $R^1$ is pentyl, heptyl, decyl, dodecyl, cyclopropylmethyl, cyclohexylmethyl, or cyclohexylpropyl;
  $R^2$ and $R^3$ together with the atoms carrying them form an isopropylidene group;
  $R^4$ is hydrogen or a methyl group; and
  X and Ar together form a group selected from the group consisting of 2-pyridinyl. 4-pyridinyl. 2 pyridinylmethyl, 3-pyridinylmethyl, 2-pyridinylethyl 2-furanylmethyl, 2-chlorophenyl, 1,2,3,4-tetrahydroisoquinolinyl, (2-fluorophenyl)methyl, (4-fluorophenyl)methyl. 4-pyridinylmethyl, (2-methoxyphenyl)methyl, (3-methoxyphenyl)methyl, (4-methoxyphenyl)methyl, 2-(4-methoxyphenyl)ethyl, 3-(N-imidazolyl)propyl, (4-chlorophenyl)methyl, (3-chlorophenyl)methyl, (2-chlorophenyl)methyl, 2-(2-chlorophenyl)ethyl, 2-(3-chlorophenyl)ethyl, 2-(4- chlorophenyl)ethyl, (3-fluorophenyl)methyl, (4-fluorophenyl)methyl, (4-bromophenyl)methyl, (2-trifluoromethylphenyl)methyl, (3-trifluoromethylphenyl)methyl, (4-trifluoromethylphenyl)methyl, (4-trifluoromethoxyphenyl)methyl, (2.4-dichlorophenyl)methyl, (2,4-difluorophenyl)methyl, (2,6-difluorophenyl)methyl, (3.4-difluorophenyl)methyl, (3,4-dichlorophenyl)methyl, (2,3-dimethoxyphenyl)methyl, 2-pyridinylmethyl, phenylmethyl, 4-(1-benzyl)piperidinyl, 2-thienylmethyl, (3-phenylpropyl), (1-methyl-3-phenyl)propyl, 2-(1-methyl-1H-pyrrol-2-yl)ethyl, 1,3-benzodioxol-5-ylmethyl, 1-naphthylmethyl and (3,5-dimethoxyphenyl)methyl;

or a physiologically acceptable salt thereof.

10. A 6-deoxy, 6-amino derivative of glucose of claim 9, or a physiologically acceptable salt thereof, selected from 1,2-O-isopropylidene-3-O-decyl-6-deoxy-6-N-(1,2,3,4-tetrahydroisoquinolinyl )-α,D-glucofuranose, 1,2-O-isopropylidene-3-O-decyl-6-deoxy-6-N-[[(3,4-difluorophenyl)methyl]amino]-α,D-glucofuranose, 1,2-O-isopropylidene-3-O-heptyl-6-deoxy-6-N-[[(2-fluorophenyl)methyl]amino]-α,D-glucofuranose, 1,2-O-isopropylidene-3-O-heptyl-6-deoxy-6-N-[(2-pyridinylmethyl)amino]-α,D-glucofuranose, 1,2-O-isopropylidene-3-O-heptyl-6-deoxy-6-N-[(2-pyridinylmethyl)amino]-α,D-glucofuranose hydrochloride, 1,2-O-isopropylidene-3-O-cyclohexylmethyl-6-deoxy-6-N-[(4-pyridinylmethyl)amino]-α,D-glucofuranose, 1,2-O-isopropylidene-3-O-cyclohexylmethyl-6-deoxy-6-N-[[(3-methoxyphenyl)methyl]amino]-α,D-glucofuranose, 1,2-O-isopropylidene-3-O-cyclohexylmethyl-6-deoxy-6-N-[[3-(N-imidazolyl)propyl]amino]-α,D-glucofuranose, 1,2-O-isopropylidene-3-O-dodecyl-6-deoxy-6-N-[[2-(2-pyridinyl)ethyl]amino]-α,D-glucofuranose, 1,2-O-isopropylidene-3-O-heptyl-6-deoxy-6-N-[(phenylmethyl)amino]-α,D-glucofuranose, 1,2-O-isopropylidene-3-O-heptyl-6-deoxy-6-N-[(3-pyridinylmethyl)amino]-α, D-glucofuranose, 1,2-O-isopropylidene-3-O-dodecyl-6-deoxy-6-N-[[4-(1-benzyl)piperidinyl]amino]-α,D-glucofuranose, 1,2-O-isopropylidene-3-O-dodecyl-6-deoxy-6-N-[[(2-trifluoromethylphenyl)methyl]amino]-α,D-glucofuranose, 1,2-O-isopropylidene-3-O-dodecyl-6-deoxy-6-N-[[(4-trifluoromethylphenyl)methyl]amino]-α,D-glucofuranose, 1,2-O-isopropylidene-3-O-dodecyl-6-deoxy-6-N-[[(3-trifluoromethylphenyl)methyl]amino]-α,D-glucofuranose, 1,2-O-isopropylidene-3-O-dodecyl-6-deoxy-6-N-[[2-(3-chlorophenyl)ethyl]amino]-α,D-glucofuranose, 1,2-O-isopropylidene-3-O-dodecyl-6-deoxy-6-N-[[2-(4-chlorophenyl)ethyl]amino]-α,D-glucofuranose, 1,2-O-isopropylidene-3-O-dodecyl-6-N-[[2-(2-chlorophenyl)ethyl]amino]-α,D-glucofuranose, 1,2-O-isopropylidene-3-O-heptyl-6-N-[[(2-methoxyphenyl)methyl]amino]-α,D-glucofuranose, 1,2-O-isopropylidene-3-O-heptyl-6-N-[[(3-methoxyphenyl)methyl]amino]-α,D-glucofuranose, 1,2-O-isopropylidene-3-O-heptyl-6-N-[[(4-methoxyphenyl)methyl]amino]-α,D-glucofuranose, 1,2-O-isopropylidene-3-O-dodecyl-6-deoxy-6-N-[[(4-fluorophenyl)methyl]amino]-α,D-glucofuranose, 1,2-O-isopropylidene-3-Q-dodecyl-6-deoxy,-6-N-[(2-thienylmethyl)amino]α,D-glucofuranose, 1,2-O-isopropylidene-3-O-heptyl-6-deoxy-6-N-[[(3-fluorophenyl)methyl]amino]-α,D-glucofuranose, 1,2-O-isopropylidene-3-O-heptyl-6-deoxy-6-N-[[2-(4-methoxyphenyl)ethyl]amino]-α,D-glucofuranose, 1,2-O-isopropylidene-3-O-heptyl-6-deoxy-6-N-[[(3-chlorophenyl)methyl]amino]-α,D-glucofuranose, 1,2-O-isopropylidene-3-O-heptyl-6-deoxy-6-N-[[(4-chlorophenyl)methyl]amino]-α,D-glucofuranose, 1,2-O-isopropylidene-3-O-heptyl-6-deoxy-6-N-[[(2-chlorophenyl)methyl]amino]-α,D-glucofuranose, 1,2-O-isopropylidene-3-O-cyclohexylmethyl-6-deoxy-6-N-[(phenylmethyl)amino]-α,D-glucofuranose, 1,2-O-isopropylidene-3-O-heptyl-6-deoxy-6-N-[(3-phenylpropyl)amino]-α,D-glucofuranose, 1,2-O-isopropylidene-3-O-heptyl-6-deoxy-6-N-[[(1-methyl-3-phenyl)propyl]amino]-α,D-glucofuranose, 1,2-O-isopropylidene-3-O-heptyl-6-deoxy-6-N-[[2-(1-methyl-1H-pyrrol-2-yl)ethyl]amino]-α,D-glucofuranose, 1,2-O-isopropylidene-3-O-cyclohexylmethyl-6-deoxy-6-N-[[(4-fluorophenyl)methyl]amino]-α,D-glucofuranose, 1,2-O-isopropylidene-3-O-cyclohexylmethyl-6-deoxy-6-N-[(2-pyridinylmethyl)amino]-α,D-glucofuranose, 1,2-O-isopropylidene-3-O-decyl-6-deoxy-6-N-[(1,3-benzodioxol-5-ylmethyl)amino]-α,D-glucofuranose, 1,2-O-isopropylidene-3-O-heptyl-6-deoxy-6-N-[[(2,4-dichlorophenyl)methyl]amino]-α,D-glucofuranose, 1,2-O-isopropylidene-3-O-heptyl-6-deoxy-6-N-[[(2,3-dimethoxyphenyl)methyl]amino]-α,D-glucofuranose, 1,2-O-isopropylidene-3-O-heptyl-6-deoxy-6-N-[[(3,5-dimethoxyphenyl)methyl]amino]-α,D-glucofuranose, 1,2-O-isopropylidene-3-O-decyl-6-deoxy-6-N-[[(3,4-dichlorophenyl)methyl]amino]-α,D-glucofuranose, 1,2-O-isopropylidene-3-O-decyl-6-deoxy-6-N-[[(2,6-difluorophenyl)methyl]amino]-α,D-glucofuranose, 1,2-O-isopropylidene-3-O-(3'-cyclohexylpropyl)-6-deoxy-6-N-[(2-pyridinylmethyl) amino]-α,D-glucofuranose, 1,2-O-isopropylidene-3-O-(3'-cyclohexylpropyl)-6-deoxy-6-N-[[(2-chlorophenyl)methyl]amino]-α,D-glucofuranose, 1,2-O-isopropylidene-3-O-cyclohexylmethyl-6-deoxy-6-N-[[(2-chlorophenyl)methyl]amino]-α,D-glucofuranose, 1,2-O-isopropylidene-3-O-cyclohexylmethyl-6-deoxy-6-N- [[(3-chlorophenyl)methyl]amino]-α,D-glucofuranose, 1,2-O-isopropylidene-3-O-cyclohexylmethyl-6-deoxy-6-N-(1,2,3,4-tetrahydroisoquinolinyl)-α,D-glucofuranose, 1,2-O-isopropylidene-3-O-cyclohexylmethyl-6-deoxy-6-N-[(2-thienylmethyl)amino]-α,D-glucofuranose, 1,2-O-isopropylidene-3-O-cyclohexylmethyl-6-deoxy-6-N-[(1-naphthylmethyl)amino]-α,D-glucofuranose, 1,2-O-isopropylidene-3-O-pentyl-6-deoxy-6-N-[(2-pyridinylmethyl)amino]-α,D-glucofuranose, 1,2-O-isopropylidene-3-O-pentyl-6-deoxy-6-N-[[(2-chlorophenyl)methyl]amino]-α,D-glucofuranose, 1,2-O-isopropylidene-3-O-pentyl-6-deoxy-6-N-[[(3-chlorophenyl)methyl]amino]-α,D-glucofuranose, 1,2-O-isopropylidene-3-O-cyclopropylmethyl-6-deoxy-6-N-[[(2-chlorophenyl)methyl]amino]-α,D-glucofuranose, 1,2-O-isopropylidene-3-O-cyclopropylmethyl-6-deoxy-6-N-[[(3-chlorophenyl)methyl]amino]-α,D-glucofuranose, 1,2-O-isopropylidene-3-O-cyclohexylmethyl-6-deoxy-6-N-[[(4-chlorophenyl)methyl]amino]-α,D-glucofuranose, 1,2-O-isopropylidene-3-O-cyclohexylmethyl-6-deoxy-6-N-[[(4-trifluoromethylphenyl)methyl]amino]-α,D-glucofuranose, 1,2-O-isopropylidene-3-O-cyclohexylmethyl-6-deoxy-6-N-[[(3-fluorophenyl)methyl]amino]-α,D-glucofuranose, 1,2-O-isopropylidene-3-O-pentyl-6-deoxy-6-N-[[(4-fluorophenyl)methyl]amino]-α,D-glucofuranose, 1,2-O-isopropylidene-3-O-cyclohexylmethyl-6-deoxy-6-N-[[(4-fluorophenyl)methyl]amino]-α,D-glucofuranose, 1,2-O-isopropylidene-3-O-heptyl-6-deoxy-6-N-[[(4-fluorophenyl)methyl]amino]-α,D-glucofuranose, 1,2-O-isopropylidene-3-O-cyclopropylmethyl-6-deoxy-6-N-[[(4-fluorophenyl)methyl]amino]-α,D-glucofuranose, 1,2-O-isopropylidene-3-O-(3'-cyclohexylpropyl)-6-deoxy-6-N-[[(4-fluorophenyl)methyl]amino]-α,D-glucofuranose, 1,2-O-isopropylidene-3-O-cyclohexylmethyl-6-deoxy-6-N-[[(2,4-difluorophenyl)methyl]amino]-α,D-glucofuranose, 1,2-O-isopropylidene-3-O-cyclohexylmethyl-6-deoxy-6-N-[[(4-trifluoromethoxyphenyl)methyl]amino]-α,D-glucofuranose, 1,2-O-isopropylidene-3-O-heptyl-6-deoxy-6-N-(4-pyridinylamino)-α,D-glucofuranose, 1,2-O-isopropylidene-3-O-heptyl-6-deoxy-6-N-[(2-chlorophenyl)amino]-α,D-glucofuranose, 1,2-O-isopropylidene-3-O-cyclohexylmethyl-6-deoxy-6-N-[[(3,4-difluorophenyl)methyl]amino]-α,D-, glucofuranose, 1,2-O-isopropylidene-3-O-cyclohexylmethyl-6-deoxy-6-N-[[(4-bromophenyl)methyl]amino]-α,D-glucofuranose, 1,2-O-isopropylidene-3-O-cyclohexylmethyl-6-deoxy-6-N-[(4-pyridinylmethyl) amino]-α,D-glucofuranose hydrochloride, 1,2-O-isopropylidene-3-O-cyclohexylmethyl-6-deoxy-6-N-[[(3-methoxyphenyl)methyl]amino]-α,D-glucofuranose hydrochloride, 1,2-O-isopropylidene-3-O-heptyl-6-deoxy-6-N-[[(2-chlorophenyl)methyl]amino]-α,D-glucofuranose hydrochloride, 1,2-O-isopropylidene-3-O-heptyl-6-deoxy-6-N-[[(3-chlorophenyl)methyl]amino]-α,D-glucofuranose hydrochloride, 1,2-O-isopropylidene-3-O-cyclohexylmethyl-6-deoxy-6-N-[[(4-fluorophenyl)methyl]amino]-α,D-glucofuranose hydrochloride, and 1,2-O-isopropylidene-3-O-cyclohexylmethyl-6-deoxy-6-N-[(2-pyridinylmethyl)amino]-α,D-glucofuranose hydrochloride.

11. A compound of claim 9, wherein the compound is 1,2-O-isopropylidene-3-O-heptyl-6-deoxy-6-N-[(2-pyridinylmethyl)amino]-α,D-glucofuranose hydrochloride.

12. A pharmaceutical composition for the treatment of an inflammatory and/or autoimmune disorder comprising an effective amount of a compound according to claim 9, or a physiologically acceptable salt thereof, and a pharmaceutically acceptable carrier.

13. A method of treating an animal or human suffering from an inflammatory and/or autoimmune disorder comprising administering thereto the compound according to claim 9, or a physiologically acceptable salt thereof, in an amount effective to treat an inflammatory and/or autoimmune disorder.

14. A method of claim 13, wherein the inflammatory and/or autoimmune disorder treated is rheumatoid arthritis, psoriasis, psoriatic arthritis, scleroderma, systemic lupus erythematosus, multiple sclerosis, inflammatory bowel disease, osteoarthritis, or asthma.

15. A compound of claim 9, wherein the compound is 1,2-O-isopropylidene-3-O-cyclohexylmethyl-6-deoxy-6-N-[[(3-methoxyphenyl)methyl]amino]-α,D-glucofuranose hydrochloride.

16. A compound of claim 9, wherein the compound is 1,2-O-isopropylidene-3-O-heptyl-6-deoxy-6-N-[[(2-chlorophenyl)methyl]amino]-α,D-glucofuranose hydrochloride.

17. A compound of claim 9, wherein the compound is 1,2-O-isopropylidene-3-O-heptyl-6-deoxy-6-N-[[(3-chlorophenyl)methyl]amino]-α,D-glucofuranose hydrochloride.

18. A compound of claim 9, wherein the compound is 1,2-O-isopropylidene-3-O-cyclohexylmethyl-6-deoxy-6-N-[[(4-fluorophenyl)methyl]amino]-α,D-glucofuranose hydrochloride.

19. A compound of claim 9, wherein, the compound is 1,2-O-isopropylidene-3-O-cyclohexylmethyl-6-deoxy-6-N-[(2-pyridinylmethyl)amino]-α,D-glucofuranose hydrochloride.

* * * * *